United States Patent
Kobus et al.

(10) Patent No.: US 9,433,644 B2
(45) Date of Patent: Sep. 6, 2016

(54) FORMULATIONS AND METHODS FOR TREATING ORAL INFLAMMATION, INJURY, OR PAIN

(71) Applicant: Invado Pharmaceuticals, LLC, Chicago, IL (US)

(72) Inventors: Edward D. Kobus, Pomona, NY (US); Bartholomew Weldon, Chicago, IL (US)

(73) Assignee: Rutgilli Pharmaceuticals, LLC, Chicago, IL (US)

( * ) Notice: Subject to any disclaimer, the term of this patent is extended or adjusted under 35 U.S.C. 154(b) by 0 days.

(21) Appl. No.: 14/340,447

(22) Filed: Jul. 24, 2014

(65) Prior Publication Data
US 2015/0030694 A1 Jan. 29, 2015

Related U.S. Application Data

(60) Provisional application No. 61/858,427, filed on Jul. 25, 2013.

(51) Int. Cl.

| | | |
|---|---|---|
| *A61F 13/02* | (2006.01) | |
| *A61K 33/42* | (2006.01) | |
| *A61K 33/14* | (2006.01) | |
| *A61Q 11/00* | (2006.01) | |
| *A61K 33/00* | (2006.01) | |
| *A61K 47/02* | (2006.01) | |
| *A61K 9/00* | (2006.01) | |
| *A61K 47/32* | (2006.01) | |
| *A61K 47/36* | (2006.01) | |
| *A61K 47/38* | (2006.01) | |

(52) U.S. Cl.
CPC .............. *A61K 33/42* (2013.01); *A61K 9/006* (2013.01); *A61K 33/00* (2013.01); *A61K 33/14* (2013.01); *A61K 47/02* (2013.01); *A61K 47/32* (2013.01); *A61K 47/36* (2013.01); *A61K 47/38* (2013.01); *A61Q 11/00* (2013.01)

(58) Field of Classification Search
CPC ..................... A61K 9/006; A61Q 11/00
See application file for complete search history.

(56) References Cited

U.S. PATENT DOCUMENTS

| | | |
|---|---|---|
| 4,024,237 A | 5/1977 | Eichel et al. |
| 4,716,035 A | 12/1987 | Sampathkumar |
| 4,738,842 A | 4/1988 | Dow et al. |
| 4,851,393 A | 7/1989 | Rha et al. |
| 5,219,486 A | 6/1993 | Ahmed et al. |
| 5,268,167 A | 12/1993 | Tung |
| 5,427,768 A | 6/1995 | Tung |
| 5,458,879 A | 10/1995 | Singh et al. |
| 5,540,913 A | 7/1996 | Turner |
| 5,989,535 A | 11/1999 | Nayak |
| 5,993,785 A | 11/1999 | Johansen et al. |
| 6,176,910 B1 | 1/2001 | Miyazaki et al. |
| 6,375,963 B1 | 4/2002 | Repka et al. |
| 6,387,352 B1 | 5/2002 | Johansen et al. |
| 7,544,348 B2 | 6/2009 | Jacob et al. |
| 7,547,433 B2 | 6/2009 | Jacob et al. |
| 7,803,392 B2 | 9/2010 | Mumper et al. |
| 2002/0142042 A1 | 10/2002 | Mumper et al. |
| 2003/0095931 A1 | 5/2003 | Stier |
| 2003/0098438 A1 | 5/2003 | Haslin |
| 2003/0185907 A1 | 10/2003 | Krumhar |
| 2004/0013695 A1 | 1/2004 | Vande-Velde |
| 2005/0281862 A1 | 12/2005 | Karakelle et al. |
| 2006/0074108 A1 | 4/2006 | Gupta |
| 2006/0140885 A1 | 6/2006 | Gaffar et al. |
| 2006/0159632 A1 | 7/2006 | Ishibashi et al. |
| 2008/0299050 A1 | 12/2008 | Bortz et al. |
| 2009/0124554 A1 | 5/2009 | Dugger, III |
| 2009/0130232 A1* | 5/2009 | Zahra ........................... 424/690 |
| 2011/0086108 A1 | 4/2011 | Weldon |
| 2012/0035216 A1* | 2/2012 | Palmer et al. ................ 514/326 |
| 2012/0251590 A1 | 10/2012 | Cruz et al. |

FOREIGN PATENT DOCUMENTS

WO 0050078 A1 8/2000

OTHER PUBLICATIONS

L.G. Corral et al., "Antimicrobial Activity of Sodium Bicarbonate", Journal of Food Science, May-Jun. 1988 vol. 53(3), 981-982, Institute of Food Technologists, Chicago, USA.
W. Carl et al., "Management of oral mucositis during local radiation and systemic chemotherapy: A study of 98 patients", The Journal of Prosthetic Dentistry, Sep. 1991, vol. 66(3), 361-369.
AS Papas et al., "A prospective, randomized trial for the prevention of mucositis in patients undergoing hematopoietic stem cell transplantation", Bone Marrow Transplantation, 2003, 31, 705-712, Nature Publishing Group.
K. Dass et al., "Efficacy of NeutraSal® (Supersaturated Calcium Phosphate Rinse) in the Prevention and Treatment of Chemotherapy and/or Radiotherapy-induced Oral Mucositis" Abstract 40160: American Radium Society, 94th Annual Meeting, May 2012.

(Continued)

*Primary Examiner* — Carlos Azpuru
(74) *Attorney, Agent, or Firm* — Neal, Gerber & Eisenberg LLP

(57) ABSTRACT

The present invention generally relates to formulations and methods for treating oral inflammation, oral injury and/or oral pain by applying hydrogel, viscous liquid, or other formulation to the oral cavity. Wet formulations comprise a hydrophilic polymer selected from the group consisting of pyrrolidones, hyaluronic acid and salts thereof, alginic acid and salts thereof, and carrageenans and salts thereof; calcium salts or ions, phosphate salts or ions, and water as well as other optional components. Dry formulations such as powders are also contemplated.

17 Claims, No Drawings

(56) References Cited

OTHER PUBLICATIONS

J. Fitz, "The Efficacy of NeutraSal® in patients with medication—induced xerostomia", accepted for presentation and poster at the 2011 Family Medicine Education Consortium: NE Region Meeting.

"NeutraSal®: A Case Study", Accepted for Abstract Presentation: The 93rd Annual Meeting of the American Radium Society, May 2011.

"NeutraSal®: A Case Study", Accepted for Abstract Presentation: 36th Annual ONS Congress, Apr. 2011.

"Efficacy of a Supersaturated Calcium Phosphate Oral Rinse (NeutraSal®) in the Treatment of Xerostomia Secondary to Sjögren's Syndrome", Sjögren's Syndrome Pilot Protocol, accepted for poster at the 2011 ACR/ARHP Annual Scientific Meeting, Nov. 11, 2011, Chicago, USA.

MuGard™ Full Prescribing Information, Sep. 2010.

NeutraSal® Labeling—Apr. 2011.

Caphosol® Labeling—Jul. 2009.

Certificates of Analysis by Microbac Laboratories, Inc., Apr. 9, 2010.

Section 510(k) Summary and Food and Drug Administration Letter issuing substantial equivalence determination—Sep. 2, 2009.

International Search Report and Written Opinion of the International Search Authority for PCT/US2014/048084, mailed Oct. 31, 2014.

Preliminary Amendment regarding U.S. Appl. No, 12/605,455, filed electronically on Feb. 15, 2012.

Non-Final Office Action regarding U.S. Appl. No. 12/605,455, mailed Feb. 29, 2012.

Final Office Action regarding U.S. Appl. No. 12/605,455, mailed Aug. 3, 2012.

* cited by examiner

FORMULATIONS AND METHODS FOR TREATING ORAL INFLAMMATION, INJURY, OR PAIN

PRIORITY

This application claims the benefit of U.S. Provisional Application No. 61/858,427, filed Jul. 25, 2013, which is hereby incorporated by reference in its entirety.

FIELD OF THE INVENTION

The present invention generally relates to formulations and methods for treating oral injury, oral inflammation, or oral pain by applying a wet formulation to the oral cavity.

BACKGROUND OF THE INVENTION

Human saliva plays a number of roles in the oral cavity, including aiding in the prevention and healing of infections in the mouth and the remineralization of teeth. Among the components found within human saliva are high concentrations of calcium and phosphate. It is believed that calcium plays a role in preventing oral infection, protecting the oral mucosa and healing wounds in the mouth. Phosphate helps to modulate pH balance in the mouth, protecting the teeth and repairing mucosal damage.

Oral mucositis is a frequent adverse effect from chemotherapy or radiation therapy. Mucositis is painful and can limit adequate nutritional intake and decrease the willingness of patients to continue treatment. More severe mucositis with extensive ulceration may require costly hospitalizations with parenteral nutrition and narcotics. Mucositis may result in serious health complications in addition to the issues for which chemotherapy or radiation was being administered. A mucosal surface that is damaged increases the risk of a secondary infection and may even prove to be an entry point for systemic infection. Mucositis may result in the need to reduce dosage in subsequent chemotherapy cycles or to delay radiation therapy, which may ultimately affect patient response to therapy.

An oral rinse supersaturated with calcium and phosphate is effective in reducing the duration and severity of oral mucositis in patients receiving hematopoietic stem cell transplantation (Bone Marrow Transplantation (2003) 31: 705-12). In addition, sodium bicarbonate is recognized as having the beneficial effect of reducing acidity of oral fluids, diluting accumulating mucus in the oral cavity and discouraging yeast and bacterial colonization.

MuGard® is a mucoadhesive oral wound rinse available by prescription only. It is indicated for the management of oral mucositis/stomatitis (that may be caused by radiotherapy and/or chemotherapy) and all types of oral wounds (mouth sores and injuries), including aphthous ulcers/canker sores and traumatic ulcers, such as those caused by oral surgery or ill-fitting dentures or braces. The ingredients for MuGard® are purified water, glycerin, benzyl alcohol, sodium saccharin, Carbomer Homopolymer A, potassium hydroxide, citric acid, polysorbate 60 and phosphoric acid.

Caphosol® is indicated for dryness of the mouth or throat (hyposalivation, xerostomia), regardless of the cause and regardless of whether the conditions are temporary or permanent. Caphosol® is provided as Dibasic Sodium Phosphate 0.032, Monobasic Sodium Phosphate 0.009, Calcium Chloride 0.052, Sodium Chloride 0.569, Purified Water qs ad (% w/w). Caphosol® is a preparation comprising two separately pack aged aqueous solutions, a phosphate solution (Caphosol A) and a calcium solution (Caphosol B) which, when both ampule solutions are combined in equal volumes, form a solution supersaturated with respect to both calcium and phosphate ions.

NeutraSal® (supersaturated calcium phosphate rinse) is a prescription mouth rinse. NeutraSal® is indicated to treat the painful symptoms associated with oral mucositis. NeutraSal® is provided as a powder for dissolving in 30 ml water to form a supersaturated calcium phosphate rinse. The powder includes sodium, phosphates, calcium, chloride, and bicarbonate.

US20110086108 involves the formulation of stable powders which, when dissolved in water form a non-pressurized carbonated solution supersaturated with calcium and phosphate ions, and also containing the presence of carbon dioxide and sodium bicarbonate. The resulting solution is used as an oral rinse for the prevention and treatment of inflammatory processes of the soft tissues of the mouth, throat and oral cavity, which may result from infection or trauma to the oral mucosal tissue.

SUMMARY OF THE INVENTION

As one aspect of the present invention, formulations are provided for treating oral injury, oral inflammation, or oral pain. The formulations comprise selected amounts of one or more hydrophilic polymers, at least one of which is selected from the group consisting of pyrrolidones, hyaluronic acid and salts thereof, alginic acid and salts thereof, carrageenans and salts thereof; celluloses; dextrins; calcium salts or ions; and phosphate salts or ions, and other excipients described herein, so as to provide a treatment having a high concentration of calcium ions and phosphate ions and that sufficient viscosity and/or adherence to oral mucosal tissues. The formulations can also include sodium bicarbonate, usually in an amount sufficient to modulate the pH balance of the oral cavity and/or control opportunistic growth of harmful bacteria in the mouth. The formulations include wet formulations such as a hydrogel, viscous liquid and/or thixotropic formulation and dry formulations such as powders that can be reconstituted with water.

As another aspect of the present invention, a method is provided for treating a subject having an oral cavity. The method comprises admitting a wet formulation as described herein in the oral cavity of the subject, wherein the subject is in need of treatment for one or more of oral injury, oral inflammation, or oral pain; moving the formulation within the oral cavity; and expelling the formulation from the oral cavity of the subject. The formulation may be admitted into the oral cavity by drinking, sipping, rubbing, or another way. The formulation may be moved within the oral cavity by swirling in the mouth, gargling, or other movement of the tongue or cheeks. The formulation may be expelled by spitting, imbibing, or another way. The formulation may coat at least a portion of the oral cavity for an extended period after the expelling step (for example, about 2 to about 60 minutes).

DETAILED DESCRIPTION

The present disclosure is based in part on a desire for an oral formulation having a high concentration of calcium ions and phosphate ions, that provides treatment of oral injury and/or oral inflammation and/or relief of pain in the oral cavity, and that has sufficient viscosity and/or adherence to oral mucosal tissues to remain in or at least partially coat the oral cavity for a period after initial administration. Formulations are provided that have such viscosity and/or adherence, and methods are provided for treating oral injury, oral inflammation and/or oral pain by administering such formulations to a subject in need of treatment. The present disclosure also relates to wet formulations and methods for preparing hydrogels, viscous liquids, and other formulations, and the use of such formulations for treating oral injury, inflammation or pain.

The present claims describe a novel method that employs dry formulations (preferably powder formulations) and mixes them in water to create an oral rinse that is supersaturated with calcium and phosphate ions. When mixed with water, the dry powder provides a wet formulation that can be used for treating of inflammation of the soft tissue of the mouth, throat, or oral cavity. The wet formulation treats inflammation by providing components within saliva that promote the health of the oral cavity, and delivering them in an oral rinse at ultra-high concentrations. The wet formulation can to accelerate a natural healing process in the oral cavity.

The present claims provide advantages which are not found in currently available commercial products, nor are those advantages taught or suggested by those products or the cited prior art. The present formulations include a stable powder containing calcium salts, phosphate salts, and chloride salts, which can be mixed in a suitable amount water (for example, from 1 to 20 times the weight of the dry formulation (powder)), thereby forming a solution supersaturated with both calcium and phosphate ions. For example, a suitable amount of water may be 10 ml to 100 ml, alternatively 20 ml to 50 ml, alternatively 30 ml. The dry formulation can be a powder having a particle size range from about 0.1 to 1,000 microns, alternatively from about 0.1 to 10 microns, alternatively from 50 to 1,000 microns. The dry formulation can have a moisture content less than about 20%, alternatively less than about 15%, alternatively less than about 10% before reconstitution with water.

The present invention provides formulations and methods that can be used to treat inflammatory processes of the soft tissues of the mouth, throat and oral cavity. Some embodiments of this solid powder mix contain a stable mixture of one or more hydrophilic polymers, calcium salts, phosphate salts, and chloride salts, all in selected concentrations to provide a surprisingly effective treatment. When water is added to these powders, the solids will dissolve rapidly to create a solution supersaturated with respect to calcium and phosphate ions.

The present formulations and methods provide an oral rinse that contains significantly higher concentrations of calcium and phosphate ions than normally found in saliva. In some embodiments, the oral treatment is supersaturated with calcium and phosphate ions at levels at least 20 times the levels found in normal, human saliva, alternatively at least 50 times, alternatively at least 100 times, alternatively at least 500 times, alternatively at least 1,000 times, alternatively at least 5,000 times, alternatively at least 10,000 times the levels found in normal, human saliva.

The present formulations and methods can provide higher concentrations of calcium and phosphate, a difference made possible by providing a stable powder to be mixed with water, in contrast to commercially available products. For example, the present formulations and methods can provide an aqueous formulation having a minimum calcium concentration of 500 ppm in distilled water, alternatively 1,000 ppm, alternatively 5,000 ppm, alternatively 10,000 ppm, alternatively 15,000 ppm, alternatively 20,000 ppm, alternatively 22,500 ppm, alternatively 25,000 ppm, alternatively 27,500 ppm, alternatively 30,000 ppm. Alternatively or additionally, the present formulations and methods can provide an aqueous formulation having a maximum calcium concentration of 100,000 ppm in distilled water, alternatively 75,000 ppm, alternatively 60,000 ppm, alternatively 50,000 ppm, alternatively 45,000 ppm, alternatively 42,500 ppm, alternatively 40,000 ppm, alternatively 37,500 ppm, alternatively 35,000 ppm. Any of the foregoing minima and maxima can be combined to form a range, provided that the maximum end of the range is higher than the minimum. Similarly, the present formulations and methods can provide an aqueous formulation having a minimum phosphate concentration of 100 ppm in distilled water, alternatively 200 ppm, alternatively 500 ppm, alternatively 1,000 ppm, alternatively 2,000 ppm, alternatively 5,000 ppm, alternatively 7,500 ppm, alternatively 10,000 ppm, alternatively 12,000 ppm, alternatively 14,000 ppm, alternatively 16,000 ppm, alternatively 18,000 ppm, alternatively 20,000 ppm. Alternatively or additionally, the present formulations and methods can provide an aqueous formulation having a maximum phosphate concentration of 50,000 pm in distilled water, alternatively 45,000 ppm, alternatively 40,000 ppm, alternatively 35,000 ppm, alternatively 32,500 ppm, alternatively 30,000 ppm, alternatively 27,500 ppm, alternatively 25,000 ppm, alternatively 22,500 ppm. Any of the foregoing minima and maxima can be combined to form a range, provided that the maximum end of the range is higher than the minimum. The calcium concentrations may be of elemental calcium, calcium compounds, calcium ions, or a mixture thereof. Likewise, the potassium concentrations may be of phosphate compounds, phosphate ions, or a mixture thereof.

An advantage of the present dry formulations is that they can be mixed with water sources other than purified or distilled water. The solid powders can be mixed with different water sources (for example, tap water and bottled water), and still provide ultra-high concentrations of calcium and phosphate. When combined with tap water, the concentration of calcium and phosphate ion will be slightly different than when measured in distilled water. The delivery through a powder allows for the creation of an oral rinse that achieves far higher levels of calcium and phosphate than can otherwise be achieved when delivered in liquid containing calcium and phosphate.

The present formulations comprise one or more hydrophilic polymers, at least one of which is selected from the group consisting of: pyrrolidones, hyaluronic acids and salts thereof, alginic acids and salts thereof, carrageenans and salts thereof, dextrins, celluloses, and mixtures thereof; a calcium salt or calcium ions; a phosphate salt or phosphate ions; and water. Other solutes found to be naturally occurring in saliva can also be included, along with flavoring and preservatives. The components of the formulation are food-grade ingredients (including but not limited to a food-grade hydrophilic polymer(s)) or pharmaceutical grade ingredients. The present formulations can also include a pH buffering agent, such as sodium bicarbonate, bicarbonate ions, or carbonate ions. The present formulations can also include an analgesic. The present formulations can also include a fluoride salt or fluoride ions, and/or a strontium salt or strontium ions. The present formulations can also one or more preservatives, antihistamines, corticosteroids, anti-microbial agents, and/or anti-fungal agents. The present formulations can further comprise a surfactant, a fragrance, a flavorant, adhesive agent, or other excipients described herein.

The present wet formulations can include one or more hydrophilic polymers, including but not limited to, pyrrolidones, hyaluronic acids and salts thereof, alginic acids and salts thereof, carrageenans and salts thereof, dextrins, celluloses, and mixtures thereof. The pyrrolidones, hyaluronic acids and salts thereof, alginic acids and salts thereof, carrageenans and salts thereof, dextrins, celluloses, and mixtures thereof in the present wet formulations is present in an amount from 0.1% to 7% by weight, alternatively from 0.1% to 6% by weight, alternatively from 0.5% to 5.5% by weight, alternatively from 1% to 3.3% by weight, based on the total weight of the wet formulation. Alternatively the amounts of water and hydrophilic polymer can be accordingly to suitable weight ratios, such as a water:(pyrrolidones, hyaluronic acids and salts thereof, alginic acids and salts thereof, carrageenans and salts thereof, dextrins, celluloses, and mixtures thereof) ratio of from 99:1 to 0.01:1, alternatively from 95:1 to 0.05:1, alternatively from 10:1 to 0.25:1.

The present dry formulations can include one or more hydrophilic polymers, including but not limited to, pyrrolidones, hyaluronic acids and salts thereof, alginic acids and salts thereof, carrageenans and salts thereof, dextrins, celluloses, and mixtures thereof. The hydrophilic polymers in the present dry formulations are present in an amount from about 2% to about 85% by weight, alternatively from about 4% to about 80% by weight, alternatively about 75% by weight, alternatively from about 20% to 60% by weight, based on the total weight of the dry formulation. The present dry formulations do not include the water to be added in the preparation of a wet formulation for use in treatment, but may include some residual water or hydration in the polymer or other components.

Polyvinylpyrrolidone (PVP) is a water-soluble polymer made from the monomer N-vinylpyrrolidone and having repeating units of:

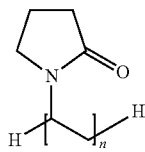

where n indicates the number of monomer repeats. PVP of various grades can be obtained from numerous commercial sources. For example, Ashland Inc. of Covington, Ky., provides the following grades of PVP having the average molecular weights in Daltons: PVP K-15 100% powder: 8,000; PVP K-15 30% solution: 8,000; PVP K-30 100% powder: 60,000; PVP K-30 30% solution: 60,000; PVP K-60 45% solution: 400,000; PVP K-90 100% powder: 1,300,000; PVP K-90 20% solution: 1,300,000; and PVP K-120 100% powder: 3,000,000. The average molecular weight of the polymer will cause it to have different effects on the viscosity of a liquid into which it is incorporated. In some embodiments of the present wet formulations, when the hydrophilic polymer is polyvinylpyrrolidone thereof, it is present in an amount from 1.5% to 11% by weight, alternatively from 3.1% to 5.5% by weight, based on the total weight of the wet formulation. In some embodiments of the present dry formulations, when the hydrophilic polymer is polyvinylpyrrolidone thereof, it is present in an amount greater than 10%, alternatively from 20% to 60% by weight, based on the total weight of the dry formulation.

Sodium alginate is the sodium salt of alginic acid. Pharmaceutical grade sodium alginate is available from Nova-Matrix, a business unit of FMC Biopolymer. Alginic acid is an anionic polysaccharide found in the cell walls of brown algae, where it forms a viscous gum through binding with water. Alginic acid has the general chemical structure:

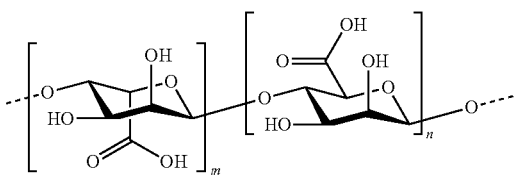

where m and n indicate the number of monomer repeats. Like the polymers discussed here, a variety of grades of sodium alginate having different average molecular weights and concentrations can be used, with a desired effect on viscosity of the formulation. Preferred grades of sodium alginate include food grade or pharmaceutical grade. In some embodiments of the present wet formulations, when the hydrophilic polymer is alginic acid or a salt thereof, it is present in an amount from 0.5% to 6.4% by weight, alternatively from 1.0% to 3.2% by weight, based on the total weight of the wet formulation. In some embodiments of the present dry formulations, when the hydrophilic polymer is polyvinylpyrrolidone thereof, it is present in a concentration from 3.5% to 88% by weight, alternatively from 7% to 44% by weight, based on the total weight of the dry formulation.

Sodium hyaluronate is the sodium salt of hyaluronic acid. Pharmaceutical grade sodium hyaluronate is available commercially from Lifecore Biomedical, LLC, of Chaska, Minn. It is a visco-elastic polymer and is normally found in the aqueous and vitreous humour of the human eye. Hyaluronic acid is a natural complex sugar of the glycosaminoglycan family and is a long-chain polymer containing repeating disaccharide units of Na-glucuronate-N-acetylglucosamine. Hyaluronic acid has the chemical structure:

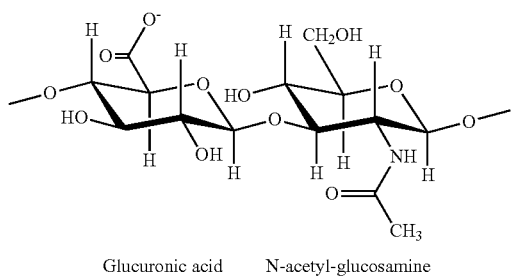

Glucuronic acid    N-acetyl-glucosamine

In some embodiments of the present wet formulations, when the hydrophilic polymer is a hyaluronic acid or salt thereof, it is present in an amount from 0.05% to 0.2% by weight, more preferably 0.1% by weight, based on the total weight of the wet formulation. In some embodiments of the present dry formulations, when the hydrophilic polymer is a hyaluronic acid or salt thereof, it is present in an amount from 0.4% to 2.8% by weight, alternatively from 0.8% to 1.4% by weight, based on the total weight of the dry formulation. In some embodiments of the formulations, sodium hyaluronate is present along with polyvinylpyrrolidone. Other salts and derivatives of hyaluronic acid can also be employed, including but not limited to potassium, calcium and mixtures thereof. The hyaluronic acid or salt can be provided in substantially pure form or in solution or mixture with other ingredients.

Carrageenans are a family of linear sulfated polysaccharides, typically extracted from red seaweeds and widely used for their gelling, thickening and stabilizing properties. Carrageenans differ in their degree and position of sulfate moieties. Preferred grades of carrageenans include SeaSpen PF available from FMC BioPolymer. In some embodiments of the present wet formulations, when the hydrophilic polymer is a carrageenan or a salt thereof, it is present in an amount from 0.25% to 4.0% by weight, alternatively from 0.5% to 3.1% by weight, alternatively about 2.17% by weight, based on the total weight of the wet formulation. In the present dry formulations, when the hydrophilic polymer is carrageenan or a salt thereof, it is preferred that it is present in an amount from 2.3% to 34% by weight, alternatively from 4.7% to 17% by weight, alternatively from 10% to 20% by weight, alternatively about 16.7% by weight, based on the total weight of the dry formulation.

In some embodiments of the wet formulations, when a hydrophilic polymer is a carrageenan or a salt thereof, it is preferred that it is present in an amount from 0.25% to 2.2% by weight, alternatively from 0.5% to 1.1% by weight, based on the total weight of the wet formulation. In some embodiments of the dry formulations, when a hydrophilic polymer is carrageenan or a salt thereof, it is preferred that it is present in an amount from 2.3% to 34% by weight, alternatively from 4.7% to 17% by weight, based on the total weight of the dry formulation.

The present formulations can include dextrins, which include maltodextrins and other malto-oligosaccharide products. A particularly suitable maltodextrin for use in the present formulations is Maltrin® QD M580, marketed by Grain Processing Corporation (Muscatine, Iowa). In some embodiments of the wet formulation, a maltodextrin or other malto-oligosaccharide product(s) is present in an amount of from 2% to 9% by weight, alternatively from 3.0% to 5.0% by weight, alternatively about 4.35% by weight, based on the total weight of the wet formulation. In some embodiments of the dry formulation, a maltodextrin or other malto-oligosaccharide product(s) is present in an amount of from 20% to 45% by weight, alternatively from 30% to 35% by weight, alternatively about 33.3% by weight, based on the total weight of the dry formulation.

The present formulations can also include microcrystalline cellulose, for example, Avicel RC-591 (FMC Corp., US) or Vivapur® MCG (JRS Pharma, Germany) or other thickening, stabilizing, or suspending agents known to those skilled in the art. A particularly suitable microcrystalline cellulose for use in the present formulations is Vivapur® MCG 611 P. In preferred embodiments of the wet formulation, a microcrystalline cellulose is present in an amount of from 1.0% to 7.0% by weight, alternatively from 2.0% to 4.0% by weight, alternatively about 3.23% by weight, based on the total weight of the wet formulation. In preferred embodiments of the dry formulation, a microcrystalline cellulose is present in an amount of from 15% to 35% by weight, alternatively from 20% to 30% by weight, alternatively from 23% to 27% by weight, alternatively about 24.7% by weight, based on the total weight of the dry formulation.

In some embodiments, the wet formulation comprises a maltodextrin in an amount from 2% to 9% by weight, alternatively about 4% to 5% by weight; a carrageenan or a salt thereof, in an amount from 1% to 4% by weight, alternatively from about 2% to 3% by weight; and a microcrystalline cellulose, in an amount from 1.5% to 7% by weight, alternatively from 2.5% to 5% by weight, wherein the weight percentages are based on total weight of the wet formulation.

Suitable sweeteners preferably are calorie-free and include xylitol, sucralose, acesulfame potassium (also known as Acesulfame K or Ace K), stevia, aspartame, neotame, and saccharin.

The present formulations can include one or more chloride salts, such as sodium chloride, potassium chloride, and mixtures thereof. In preferred embodiments of the wet formulation, sodium chloride is present in a concentration of from 0.4% to 1.8% by weight, alternatively from 0.8% to 0.9% by weight, alternatively about 0.87% by weight, based on the total weight of the wet formulation. In preferred embodiments of the dry formulation, sodium chloride is present in a concentration of from 2.5% to 21% by weight, alternatively from 5% to 14% by weight, alternatively about 6.7% by weight, based on the total weight of the dry formulation.

The present formulations can include one or more calcium salts, such as include calcium chloride, calcium carbonate, calcium citrate, calcium hydroxide, and mixtures thereof. In preferred embodiments of the wet formulation, calcium chloride is present in a concentration of from 0.2% to 1%, alternatively from 0.4% to 0.5%, alternatively about 0.43% by weight, based on the total weight of the wet formulation. In preferred embodiments of the dry formulation, calcium chloride is present in a concentration of from 1.2% to 10%, alternatively from 2.5% to 7%, alternatively about 3.3% by weight, based on the total weight of the dry formulation.

The present formulations can include one or more phosphate salts, such as sodium phosphate (including monobasic, dibasic or both), potassium phosphate, and mixtures thereof. In preferred embodiments of the wet formulation, sodium phosphate monobasic is present in a concentration of from 0.05% to 0.15% by weight, alternatively 0.08% to 0.09% by weight, based on the total weight of the wet formulation. In preferred embodiments of the dry formulation, sodium phosphate monobasic is present in a concentration of from 0.25% to 2%, alternatively from 0.5% to 1.4% by weight, alternatively about 0.7% by weight, based on the total weight of the dry formulation. In preferred embodiments of the wet formulation, sodium phosphate dibasic is present in a concentration of from 0.05% to 0.15% by weight, alternatively from 0.08% to 0.09% by weight, based on the total weight of the wet formulation. In preferred embodiments of the dry formulation, sodium phosphate dibasic is present in a concentration of from 0.2% to 1.8% by weight, alternatively from 0.4% to 1.2% by weight, alternatively about 0.6% by weight, based on the total weight of the dry formulation.

The present formulations can further include fumed silica (i.e., amorphous silicon dioxide particles), for example, Aerosil® fumed silicas marketed by Evonik Industries AG. A particularly suitable fumed silica for use in the present formulations is Aerosil® 200. In preferred embodiments of the wet formulation, a fumed silica is present in a concentration of from about 0.01% to 3.0% by weight, alternatively from 0.05% to 0.15% by weight, alternatively about 0.09% by weight, based on the total weight of the wet formulation. In preferred embodiments of the dry formulation, a fumed silica is present in a concentration of from 0.25% to 2.0% by weight, alternatively from 0.5% to 1.4% by weight, alternatively about 0.7% by weight, based on the total weight of the dry formulation.

The present formulations can also include sodium bicarbonate. In preferred embodiments of the wet formulation, sodium bicarbonate is present in a concentration of from 0.05% to 5.0% by weight, alternatively from 1.0% to 3.0% by weight, alternatively about 1.74% by weight, based on the total weight of the wet formulation. In preferred embodiments of the dry formulation, sodium bicarbonate is present in a concentration of from 5% to 20% by weight, alternatively from 10% to 15% by weight, alternatively about 13.3% by weight, based on the total weight of the dry formulation.

In some embodiments of the present invention, a dry formulation can include sodium chloride, in an amount of at least 5% by weight; calcium chloride, in an amount of at least 2.5% by weight; sodium phosphate (dibasic), in an amount of at least 0.25% by weight; sodium phosphate (monobasic), in an amount of at least 0.25% by weight; a maltodextrin, in an amount from 20% to 45% by weight; carrageenan or a salt thereof, in an amount from 10% to 20% by weight; microcrystalline cellulose, in an amount from 15% to 35% by weight; fumed silica, in an amount from about 0.1% to 1.2% by weight; and/or sodium bicarbonate, in an amount from 5% to 25% by weight, wherein the weight percentages are based on total weight of the dry formulation.

In some embodiments of the present invention, the dry formulation can include a maltodextrin in an amount from about 20% to 45% by weight, alternatively from about 30% to 35% by weight; carrageenan or a salt thereof, in an amount from about 10% to 20% by weight, alternatively about 15% to 18% by weight; microcrystalline cellulose, in an amount from 20% to 30% by weight, wherein the weight percentages are based on total weight of the dry formulation.

In some embodiments of the present invention, the wet formulation can include sodium chloride in an amount of at least 0.4% by weight; calcium chloride in an amount of at least 0.2% by weight; sodium phosphate (dibasic), in an amount of at least 0.04% by weight; sodium phosphate (monobasic), in an amount of at least 0.04% by weight; a maltodextrin, in an amount from 2% to 9% by weight; a carrageenan or a salt thereof, in an amount from 1% to 4% by weight; a microcrystalline cellulose, in an amount from 1.5% to 7% by weight; fumed silica, in an amount from about 0.04% to 2% by weight; and sodium bicarbonate, in an amount from 0.8% to 3.5% by weight, wherein the weight percentages are based on total weight of the wet formulation.

In some embodiments of the present invention, the wet formulation comprises a maltodextrin in an amount from 2% to 9% by weight; carrageenan or a salt thereof, in an amount from 1% to 4% by weight; microcrystalline cellulose, in an amount from 1.5% to 7% by weight, wherein the weight percentages are based on total weight of the wet formulation.

Suitable analgesics for use in the present formulations include benzocaine, lidocaine, tetracaine, hexylcaine, bupivacaine, proparacaine, prilocaine, benoxinate, mepivacaine, propoxycaine, dyclonine, pramoxine, mepivacaine, procaine, chloroprocaine, ropivacaine, dibucaine, and etidocaine, and mixtures thereof. When the formulation includes an analgesic, one embodiment of the present methods can further include administering food to the subject after the analgesic has ameliorated oral pain or discomfort.

Suitable preservatives for use in the present formulations include preservatives or preservative systems, such as sorbic acid and its salts, benzoic acid and its salts, calcium propionate, sodium nitrite, sodium nitrate, sulfites (such as sulfur dioxide, sodium bisulfite, and potassium hydrogen sulfite), disodium EDTA, butylated hydroxyanisole (BHA), butylated hydroxytoluene (BHT), tert-butyl hydroquinone (TBHQ), and propyl gallate.

Suitable antihistamines for use in the present formulations include diphenhydramine, which can provide anti-inflammatory benefits. Suitable corticosteroids include prednisone. Diphenhydramine and/or prednisone are contemplated as preferred ingredients for providing anti-inflammatory benefits.

Suitable anti-microbial agents for use in the present formulations include clorhexidine and peroxide compounds. Suitable anti-fungal agents include nystatin and amphotericin.

The present formulations can be in the form of a hydrogel. The hydrogel can be administered to a subject in need of treatment for injury to or inflammation of the oral mucosa. The hydrogel can also include an analgesic agent, and a method of treating a subject can comprising administering such a hydrogel for treating injury to or inflammation of the oral mucosa, where pain is also present. Hydrogels contain mostly water held by hydrophilic polymer chains. The hydrophilic polymers are highly absorbent, and may be natural or synthetic polymers. SockIt!® Dermal Wound Gel is a commercially available example of a hydrogel wound dressing for oral wounds, and as such, is illustrative of a "hydrogel". The present formulations can be in the form of a viscous liquid or a thixotropic formulation.

In some embodiments, the present formulations can have a viscosity between about 5 cPs and 500,000 cPs. In some embodiments, the present formulations can have a viscosity between about 25 cPs and 10,000 cPs, alternatively between about 50 cPs and 5,000 cPs, alternatively between about 75 cPs and 1,000 cPs, alternatively about 100 cPs. All these viscosity values may be measured at 25° C. or at 37° C. as described herein. In other embodiments, the present formulations have viscosities of at least about 5,000 cPs, alternatively a viscosity in the range of from about 5,000 cPs to about 500,000 cPs, alternatively a viscosity of from about 10,000 cPs to about 100,000 cPs. Viscosity can be measured by an appropriate method or apparatus for the particular formulation. For example, the methods and apparatus described in ASTM D445-12 or in General Chapter <911> "Viscosity" of the United States Pharmacopeia (USP) can be used to measure the viscosity of various embodiments. The measurement protocol can be adapted to measure the viscosity at different temperatures. The formulations may be thixotropic, meaning they are gel-like at rest but fluid when agitated. Alternatively or additionally, the formulation can have the property of having gel-like consistency at room temperature or at 25° C. or at 37° C. and liquid-like or flowable consistency at body temperature, such as in the oral cavity of a subject.

The present disclosure also provides methods of manufacturing hydrogels, viscous liquids, and other formulations suitable for use in the treatment of oral injury, oral inflammation and/or oral pain. Suitable formulations are prepared as follows. The ingredients are combined and mixed with an appropriate volume of water to achieve the consistency desired. Preferred weight ratios of solid ingredients to water include from about 10:1 to about 0.1:1, alternatively from about 5:1 to about 0.5:1. Calcium salts, phosphate salts and/or other salts can be added as dry ingredients, or they can be pre-mixed with water to form a solution containing at least some dissociated ions. The water can be distilled water, tap water, bottled water or water from another source. The liquids or hydrogels can be packaged in a tube, sachet, or other container.

The present formulations, including the present hydrogels and viscous liquids, are designed to be physiologically compatible with both intact and compromised tissue in the mouth, and will manage pain associated with all types of injury to the mucosal tissue of the mouth and oral cavity. The pH and osmotic pressure of the formulations can be adjusted to be compatible with saliva, such as by including an appropriate amount of sodium bicarbonate, for example. Sodium bicarbonate assists in balancing the pH of a hydrogel and buffering of oral acids in the mouth.

A powder or dry formulation is also contemplated, which would be mixed with a suitable amount of water before administration to the oral cavity.

The present disclosure also provides methods for treating oral wounds, oral mucositis or other inflammation, or oral pain. The methods comprise administering a formulation as described herein, such as a hydrogel, a viscous liquid, or another wet formulation, to a subject in need of treatment. In some embodiments, the method comprises forming a wound dressing in the oral cavity, such as when applied to an oral cavity having a wound or lesion. In some embodiments, the oral inflammation, injury or pain arises from an infection to the mouth, including but not limited to candidiasis, moniliasis, reactivation of latent virus and secondary infections, septicaemia, and combinations thereof. The present methods can be used for the prevention and treatment of dysphagia and/or stomatitis. In some embodiments, the inflammation is part of the broader syndrome associated with oral mucositis, erythema, Sjogren's Syndrome and any combination thereof. The present methods can also be used for treatment of oral inflammation associated with immune-compromised patients including bone marrow transplant patients and AIDS patients, or associated with chemotherapy or radiation treatment.

In some embodiments, the present methods of treatment comprise admitting a viscous liquid, hydrogel, or other wet formulation into a mouth of a subject in need of treatment, moving the viscous liquid, hydrogel, or other formulation around the mouth (such as by swirling, swishing or gargling), and expelling the viscous liquid, hydrogel, or other formulation from the subject's mouth.

The pH and osmotic pressure of the hydrogel or other formulation can be adjusted to be compatible with saliva. Suitable pH ranges for the hydrogel comprise from 5 to 9, alternatively from 6 to 8, alternatively from 6.0 to 7.5.

With respect to the formulations described in the specification, it is intended that the specification also provides a description of methods of using any of those formulations in the described methods of use, including methods of treatment and methods of manufacture. With respect to the methods of manufacture described in the specification, it is intended that the specification also provides a description of the manufacture of any of the formulations described herein.

EXAMPLES

Example 1

Formulations containing polyvinylpyrrolidone are provided. The concentrations are provided as percentages by weight of the total formulation weight. The estimated concentrations are based on the combination of the other ingredients when mixed with an amount of water suitable for creating a wet formulation to be administered to the oral cavity. Alternatively, the formulation may be provided as a dry powder. Exemplary ranges of aqueous formulations and dry formulations are provided below.

| Ingredient | mg/dose | Concentration (aqueous formulation) | Concentration (dry formulation) |
|---|---|---|---|
| Sodium Chloride | 100 | 0.8-0.9% | 5.6-10% |
| Calcium Chloride | 50 | 0.4-0.5% | 2.8-5% |
| Sodium Phosphate, Dibasic | 9 | 0.08% | 0.4-0.8% |
| Sodium Phosphate, Monobasic | 10 | 0.08-0.09% | 0.5-1% |
| Sweetener* | 500-1000 | 4.2-9.1% | 28-98% |
| PVP K30 | 350-600 | 3.1-5.5% | 20-60% |
| Water | 10000 | 85.0-90.8% | Not applicable. |
| Total | 11019-11769 | 100% | 100% |

*preferably xylitol or Ace K.

Example 2

Formulations containing sodium hyaluronate and polyvinylpyrrolidone are provided. The concentrations are provided as percentages by weight of the total formulation weight. The estimated concentrations are based on the combination of the other ingredients when mixed with an amount of water suitable for creating a wet formulation to be administered to the oral cavity. Alternatively, the formulation may be provided as a dry powder. Exemplary ranges of aqueous formulations and dry formulations are provided below.

| Ingredient | mg/dose | Concentration (aqueous formulation) | Concentration (dry formulation) |
|---|---|---|---|
| Sodium Chloride | 100 | 0.8-0.9% | 5.6-9.6% |
| Calcium Chloride | 50 | 0.4-0.5% | 2.8-4.8% |
| Sodium Phosphate, Dibasic | 9 | 0.08% | 0.5-0.8% |
| Sodium Phosphate, Monobasic | 10 | 0.08-0.09% | 0.5-1% |
| Sweetener* | 500-1000 | 4.2-9.1% | 28-96% |
| Sodium Hyaluronate | 15 | 0.1% | 0.8-1.4% |
| PVP K30 | 360-600 | 3.1-5.4% | 20-58% |
| Water | 10000 | 84.9-90.5% | Not applicable. |
| Total | 11044-11784 | 100% | 100% |

*preferably xylitol, sucralose, or Ace K.

Example 3

Formulations containing sodium alginate is provided. The concentrations are provided as percentages by weight of the total formulation weight. The estimated concentrations are based on the combination of the other ingredients when mixed with an amount of water suitable for creating a wet formulation to be administered to the oral cavity. Alternatively, the formulation may be provided as a dry powder. Exemplary ranges of aqueous formulations and dry formulations are provided below.

| Ingredient | mg/dose | Concentration (aqueous formulation) | Concentration (dry formulation) |
|---|---|---|---|
| Sodium Chloride | 100 | 0.9% | 6.6-12.7% |
| Calcium Chloride | 50 | 0.4-0.5% | 3.3-6.3% |
| Sodium Phosphate, Dibasic | 9 | 0.08% | 0.6-1.2% |

-continued

| Ingredient | mg/dose | Concentration (aqueous formulation) | Concentration (dry formulation) |
|---|---|---|---|
| Sodium Phosphate, Monobasic | 10 | 0.09% | 0.6-1.3% |
| Sweetener* | 500-1000 | 4.3-9.3% | 32% or more |
| Sodium Alginate | 120-350 | 1.0-3.2% | 7-44% |
| Water | 10000 | 86.8-92.7% | Not applicable. |
| Total | 10789-11519 | 100% | 100% |

*preferably xylitol, sucralose, or Ace K.

Example 4

Formulations containing Carrageenan or SeaSpen PF (a combination of carrageenan NF, calcium sulfate, and trisodium phosphate) are provided. SeaSpen PF is available from FMC Biopolymer of Philadelphia, Pa. The concentrations are provided as percentages by weight of the total formulation weight. The estimated concentrations are based on the combination of the other ingredients when mixed with an amount of water suitable for creating a wet formulation to be administered to the oral cavity. Alternatively, the formulation may be provided as a dry powder. Exemplary ranges of aqueous formulations and dry formulations are provided below.

| Ingredient | mg/dose | Concentration (aqueous formulation) | Concentration (dry formulation) |
|---|---|---|---|
| Sodium Chloride | 100 | 0.9% | 7.7-14% |
| Calcium Chloride | 50 | 0.4-0.5% | 3.9-6.9% |
| Sodium Phosphate, Dibasic | 9 | 0.08% | 0.6-1.2% |
| Sodium Phosphate, Monobasic | 10 | 0.09% | 0.7-1.4% |
| Sweetener* | 500-1000 | 4.4-9.3% | 38% or more |
| Carrageenan or SeaSpen PF | 60-120 | 0.5-1.1% | 4.7-17% |
| Water | 10000 | 88.6-93.2% | Not applicable. |
| Total | 10729-11289 | 100% | 100% |

*preferably xylitol, sucralose, or Ace K.

Example 5

Formulations containing Carrageenan or SeaSpen PF are provided. SeaSpen PF is available from FMC Biopolymer of Philadelphia, Pa. The concentrations are provided as percentages by weight of the total formulation weight. In this example, approximately 10 milliliters of water would be used to reconstitute the dry formulation provided below.

| Ingredient | mg/dose | Concentration (aqueous formulation) | Concentration (dry formulation) |
|---|---|---|---|
| Sodium Chloride | 100 | 0.87% | 6.7% |
| Calcium Chloride | 50 | 0.43% | 3.3% |
| Sodium Phosphate, Dibasic | 9 | 0.08% | 0.6% |
| Sodium Phosphate, Monobasic | 10 | 0.09% | 0.7% |
| Maltrin QD M580 | 500 | 4.35% | 33.3% |
| Carrageenan or SeaSpen PF | 250 | 2.17% | 16.7% |
| Vivapur MCG 611 P | 371 | 3.23% | 24.7% |

-continued

| Ingredient | mg/dose | Concentration (aqueous formulation) | Concentration (dry formulation) |
|---|---|---|---|
| Aerosil 200 | 10 | 0.09% | 0.7% |
| Sodium Bicarbonate | 200 | 1.74% | 13.3% |
| Water | 10000 | 86.96% | Not applicable |
| Total | 11500 | 100% | 100% |

Example 6

A Brookfield viscometer is used to determine the rheological behavior of the wet formulations described oral rinse at 37±1° C. A rheogram was generated by progressively increasing RPM (upcurve) recording the % torque after each reading stabilized. The upcurve was immediately followed by a downcurve by progressively decreasingly RPM. Viscosity is calculated at each RPM, and the stress is then determined by multiplying the viscosity by the RPM. The rheological profile was generated by plotting stress (e.g., F/A) on the x-axis and the RPM (e.g., Rate of Shear) on the y-axis.

Example 7

A number of mammals are given an acute radiation dose of 40 Gy directed to their oral mucosa on day 0. Test materials (each of the above formulations of the first through fifth examples) were applied topically beginning the day before radiation (day-1) and continuing until 20 days following radiation (day 20). The grade of mucositis is scored, beginning on day 6, and for every second day thereafter, until the end of the study on day 28. The effect on mucositis of each treatment group is compared to the saline control. Each animal is scored according to a mucositis scale (0 to 5) in which 0 represents no mucositis, 5 represents severe mucositis, and a score of three or above indicating that ulceration is observed. The mean of scores of animals in each group is recorded, and the number of days hamsters in each group have severe (score >3) mucositis is calculated. Treatment efficacy is defined as a statistically significant lower number of mammals with this score in a drug treatment group, versus control as determined by chi-square analysis.

This example is expected to demonstrate that the present formulations are superior than the saline control in reducing the severity of oral mucositis.

All of the references cited herein, including patents, patent applications, and publications, are hereby incorporated in their entireties by reference.

In the present disclosure, wherever the word "comprising" is found, it is contemplated that the words "consisting essentially of" or "consisting of" may be used in its place.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

Although the dependent claims have single dependencies in accordance with U.S. patent practice, each of the features in any of the dependent claims can be combined with each of the features of other dependent claims or the main claim.

What we claim is:

1. A dry formulation adapted for reconstituting with water to form a liquid formulation for treating oral injury, oral inflammation and/or oral pain, the dry formulation comprising:
one or more hydrophilic polymers, at least one of which is selected from the group consisting of:
pyrrolidones,
hyaluronic acids and salts thereof;
alginic acids and salts thereof;
carrageenans and salts thereof;
celluloses;
dextrins;
and mixtures thereof, wherein said hydrophilic polymers are present in an amount between 4% to 85%, based on the total weight of the dry formulation;
from 2.5% to 7% by weight, based on the total weight of the dry formulation, of one or more calcium salts;
from 0.4% to 1.2% by weight, based on the total weight of the dry formulation, of one or more phosphate salts; and
sodium chloride.

2. The dry formulation of claim 1, further comprising sodium bicarbonate.

3. The dry formulation of claim 1, wherein at least one of said hydrophilic polymers includes a polyvinylpyrrolidone, sodium hyaluronate, a carrageenan, a microcrystalline cellulose and a maltodextrin.

4. The dry formulation of claim 1, wherein at least one of said hydrophilic polymers is carrageenan or a salt thereof.

5. The dry formulation of claim 4, further comprising a microcrystalline cellulose.

6. The dry formulation of claim 4, further comprising a maltodextrin.

7. The dry formulation of claim 4, wherein the dry formulation comprises a maltodextrin in an amount from 20% to 45% by weight; carrageenan or a salt thereof, in an amount from 10% to 20% by weight; microcrystalline cellulose, in an amount from 15% to 35% by weight, wherein the weight percentages are based on total weight of the dry formulation.

8. A dry formulation adapted for reconstituting with water to form a liquid formulation for treating oral injury, oral inflammation and/or oral pain, the dry formulation comprising:
one or more hydrophilic polymers, at least one of which is selected from the group consisting of:
pyrrolidones,
hyaluronic acids and salts thereof;
alginic acids and salts thereof;
carrageenans and salts thereof;
celluloses;
dextrins;
and mixtures thereof; wherein said hydrophilic polymers are present in an amount between 4% to 85%, based on the total weight of the dr formulation;
from 2.5% to 7% by weight, based on the total weight of the dry formulation, of one or more calcium salts;
from 0.4% to 1.2% by weight, based on the total weight of the dry formulation, of one or more phosphate salts;
sodium chloride, in an amount of at least 5% by weight;
calcium chloride, in an amount of at least 2.5% by weight;
sodium phosphate (dibasic), in an amount of at least 0.25% by weight;
sodium phosphate (monobasic), in an amount of at least 0.25% by weight;
a maltodextrin, in an amount from 20% to 45% by weight;
a carrageenan or a salt thereof, in an amount from 10% to 20% by weight;
a microcrystalline cellulose, in an amount from 15% to 35% by weight;
fumed silica, in an amount from about 0.1% to 1.2% by weight; and
sodium bicarbonate, in an amount from 5% to 25% by weight,
wherein the weight percentages are based on total weight of the dry formulation.

9. The dry formulation of claim 1, wherein the dry formulation comprises sodium chloride, in an amount of at least 5% by weight, wherein the weight percentages are based on total weight of the dry formulation.

10. The dry formulation of claim 1, wherein the dry formulation comprises calcium chloride, in an amount of at least 2.5% by weight, wherein the weight percentages are based on total weight of the dry formulation.

11. The dry formulation of claim 1, wherein the dry formulation comprises sodium phosphate (dibasic), in an amount of at least 0.25% by weight, wherein the weight percentages are based on total weight of the dry formulation.

12. The dry formulation of claim 1, wherein the dry formulation comprises sodium phosphate (monobasic), in an amount of at least 0.25% by weight, wherein the weight percentages are based on total weight of the dry formulation.

13. The dry formulation of claim 1, wherein the dry formulation comprises a maltodextrin, in an amount from 20% to 45% by weight, wherein the weight percentages are based on total weight of the dry formulation.

14. The dry formulation of claim 1, wherein the dry formulation comprises a carrageenan or a salt thereof, in an amount from 10% to 20% by weight, wherein the weight percentages are based on total weight of the dry formulation.

15. The dr formulation of claim 1, wherein the dry formulation comprises a microcrystalline cellulose, in an amount from 15% to 35% by weight, wherein the weight percentages are based on total weight of the dr formulation.

16. The dry formulation of claim 1, wherein the dry formulation comprises fumed silica, in an amount from about 0.1% to 1.2% by weight, wherein the weight percentages are based on total weight of the dry formulation.

17. The dry formulation of claim 1, wherein the dry formulation comprises sodium bicarbonate, in an amount from 5% to 25% by weight, wherein the weight percentages are based on total weight of the dry formulation.

* * * * *

UNITED STATES PATENT AND TRADEMARK OFFICE
CERTIFICATE OF CORRECTION

PATENT NO. : 9,433,644 B2
APPLICATION NO. : 14/340447
DATED : September 6, 2016
INVENTOR(S) : Edward D. Kobus et al.

It is certified that error appears in the above-identified patent and that said Letters Patent is hereby corrected as shown below:

In the Claims

Column 15, Line 56, in Claim 8, "dr" should be changed to --dry--.

Column 16, Line 45, in Claim 15, "dr" should be changed to --dry--.

Column 16, Line 48, in Claim 15, "dr" should be changed to --dry--.

Signed and Sealed this
Twenty-fifth Day of December, 2018

Andrei Iancu
*Director of the United States Patent and Trademark Office*